(12) United States Patent
Puppels et al.

(10) Patent No.: US 11,357,405 B2
(45) Date of Patent: Jun. 14, 2022

(54) OPTICAL PROBE FOR MEASURING A TISSUE SAMPLE

(71) Applicant: Erasmus University Medical Center Rotterdam, Rotterdam (NL)

(72) Inventors: Gerwin Jan Puppels, Schiedam (NL); Tom Christian Bakker Schut, Zoetermeer (NL); Senada Koljenovic, Rotterdam (NL); Peter Jacobus Caspers, Capelle aan den IJssel (NL)

(73) Assignee: Erasmus University Medical Center Rotterdam, Rotterdam (NL)

( * ) Notice: Subject to any disclaimer, the term of this patent is extended or adjusted under 35 U.S.C. 154(b) by 388 days.

(21) Appl. No.: 16/063,094

(22) PCT Filed: Dec. 21, 2015

(86) PCT No.: PCT/NL2015/050891
§ 371 (c)(1),
(2) Date: Jun. 15, 2018

(87) PCT Pub. No.: WO2017/111576
PCT Pub. Date: Jun. 29, 2017

(65) Prior Publication Data
US 2020/0315459 A1    Oct. 8, 2020

(51) Int. Cl.
*A61B 5/00* (2006.01)
*A61B 90/00* (2016.01)
*A61B 90/30* (2016.01)

(52) U.S. Cl.
CPC .......... *A61B 5/0084* (2013.01); *A61B 5/0075* (2013.01); *A61B 5/6848* (2013.01);
(Continued)

(58) Field of Classification Search
CPC ... A61B 5/0084; A61B 5/0075; A61B 5/6885; A61B 5/6848; A61B 2562/0238; A61B 2090/062; A61B 2090/306
See application file for complete search history.

(56) References Cited

U.S. PATENT DOCUMENTS 6,246,901 B1 * 6/2001 Benaron .............. A61B 5/0071
600/407
2004/0267121 A1 * 12/2004 Sarvazyan ......... A61B 17/3403
600/439

(Continued)

FOREIGN PATENT DOCUMENTS

CN    2 712 301       7/2005
EP    1567852 B1 *    2/2003

(Continued)

OTHER PUBLICATIONS

Caspers et al. (2001) J. Invest. Dermatol. 116(3):434-442 "In Vivo Concoal Raman Microspectroscopy of the Skn: Noninvasive Determination of Molecular Concentration Profiles".

(Continued)

*Primary Examiner* — Joseph M Santos Rodriguez
*Assistant Examiner* — Kaitlyn E Selmer
(74) *Attorney, Agent, or Firm* — Adsero IP

(57) ABSTRACT

An optical probe, instrument, and method for measuring a tissue sample. The optical probe comprises a needle having a needle tip formed to penetrate a tissue surface and an optical waveguide arranged to transmit light through the needle; and a probe housing for holding the needle and comprising at least one of an actuator or a sensor configured to receive or generate a depth signal to determine a depth position of the needle tip relative to the tissue surface.

15 Claims, 7 Drawing Sheets

(52) U.S. Cl.
CPC ...... *A61B 5/6885* (2013.01); *A61B 2090/062* (2016.02); *A61B 2090/306* (2016.02); *A61B 2562/0238* (2013.01)

(56) References Cited

U.S. PATENT DOCUMENTS

| | | | |
|---|---|---|---|
| 2008/0171949 A1* | 7/2008 | Spiteri | A61B 5/418 607/115 |
| 2009/0069673 A1* | 3/2009 | Tapalian | A61B 5/407 600/425 |
| 2009/0112119 A1 | 4/2009 | Kim | |
| 2009/0221920 A1* | 9/2009 | Boppart | A61B 5/6853 600/476 |
| 2009/0326385 A1 | 12/2009 | Hendriks | |
| 2010/0317964 A1 | 12/2010 | Hendriks | |
| 2010/0331782 A1 | 12/2010 | Hendriks | |
| 2012/0059251 A1 | 3/2012 | Bakker | |
| 2014/0107569 A1 | 4/2014 | Fischer | |
| 2014/0228661 A1 | 8/2014 | Popa-Simil | |
| 2015/0150631 A1 | 6/2015 | Lee | |
| 2015/0245769 A1* | 9/2015 | Mimura | A61B 5/0084 600/477 |
| 2016/0007858 A1* | 1/2016 | Hendriks | A61B 5/0071 600/424 |
| 2016/0008057 A1* | 1/2016 | Peppou | A61B 18/02 600/327 |

FOREIGN PATENT DOCUMENTS

| | | |
|---|---|---|
| EP | 1 567 852 | 6/2007 |
| WO | WO 2014/199641 | 12/2014 |

OTHER PUBLICATIONS

International Search Report from PCT/NL2015/050891 dated Sep. 5, 2016.
Wolthuis et al. (2001) J. Anal. Chem. 73:3915-3920 "Determination of Water Concentration in Brain Tissue by Raman Spectroscopy".

* cited by examiner

OPTICAL PROBE FOR MEASURING A TISSUE SAMPLE

RELATED APPLICATIONS

This application is a 35 U.S.C. § 371 national phase application of PCT/NL2015/050891 (WO 2017/111576), filed on Dec. 21, 2015, entitled "Optical Probe for Measuring a Tissue Sample", which is incorporated herein by reference in its entirety.

TECHNICAL FIELD AND BACKGROUND

The present disclosure relates to an optical probe for measuring a tissue sample, an instrument comprising the optical probe, a method of measuring a tissue sample, and a computer readable.

Cancer is a major public health issue. Adequate tumour resection with acceptable remaining function and appearance is a main goal. Current practice of anatomy visual inspection and palpation by the surgeon, are insufficient to warrant adequate resections. In the so-called frozen section procedure the surgeon takes tissue samples from the surgical wound bed for microscopic evaluation by a pathologist. However, the procedure is laborious and time consuming and therefore limited to inspection of only a small number samples and fraught with sampling error.

Some aspects of the present disclosure may improve intra-operative inspection of resection margins on a tumour resection specimen, to assess if adequate margins have been achieved.

SUMMARY

A first aspect of the present disclosure provides an optical probe for measuring a tissue sample. The optical probe comprises a needle having a needle tip formed to penetrate a tissue surface and an optical waveguide arranged to transmit light through the needle. The optical probe further comprises a probe housing for holding the needle and at least one of an actuator or a sensor configured to receive or generate a depth signal to determine a depth position of the needle tip relative to the tissue surface.

The inventors find that tumour tissue can be distinguished from healthy tissue by means of its spectral signature, e.g. Raman spectrum. For example, in oral cancer tissue the water content is found to be higher than in healthy tissue. The optical probe allows to quickly measure the Raman spectrum at a variable controlled depth in a tissue specimen. By measuring the spectrum as a function of depth the margin of healthy tissue surrounding the tumour tissue can be determined to see if sufficient margin around the tumor has been cut out.

By using an optical fiber as waveguide inside a needle, light can be effectively transmitted to a specific controlled depth of the tissue sample. Depending on the tissue properties, a specific response spectrum can be measured by collecting the light through the same or a further optical fiber. The optical fiber may extend beyond a length of the needle to connect to an optical interrogator device. Preferably, the fiber and instrument are adapted for measuring a Raman spectrum. Accordingly, the fiber material can be particularly adapted to transmit the corresponding wavelengths. For example, the optical fiber comprises a core, a cladding and optionally a coating for transmitting light at least in a wavelength range between 600 to 1000 nanometres. Also other wavelength ranges may be used.

The depth measurement of the needle may be based e.g. on a measured displacement of the needle with respect to a reference plane. By providing the probe housing with a tissue engaging surface, the tissue surface can be determined by physical interaction with the probe. By guiding the needle transverse to the tissue engaging surface, the depth of the needle tip in the tissue may be determined by measuring and/or actuating the displacement of the needle with respect to the tissue engaging surface. For example, the needle may slide through a linear guidance. By allowing the needle to fully retract into the housing, the instrument may be more safe to handle. When the housing is brought in contact with a tissue, the needle may extend from the housing into the tissue.

By providing an actuator, movement of the needle during the measurement can be well controlled. For example, the probe may receive a depth signal as input to the actuator to provide an absolute or relative position of the needle tip with respect to the tissue surface and/or the tissue engaging surface. For example, the actuator may comprise a translation stage with a moveable stage attached to the needle and/or a needle mount. The probe housing may comprise the appropriate, e.g. electrical, wiring to transfer the depth signal to the actuator to control actuation of the depth position of the needle.

By providing a pressure sensor, a contact of the probe housing and/or the needle with the tissue surface can be detected. For example, a first pressure signal of contact between the probe housing and tissue may cause actuation of the needle. When the probe is a hand-held device a safety button can be added near a hand grip portion of the housing to prevent accidental actuation of the needle. Alternatively, or in addition, the button can be used to trigger the needle actuation instead of the pressure sensor. When no actuator is used, e.g. the button may unlock a manually operated mechanism to move the needle out of the housing.

By providing a sensor alternative or in addition to an actuator, the depth position of the needle tip may be measured. For example, the depth signal may be calculated from an output of the sensor. For example, the sensor may measure a translation of the needle relative to the tissue engaging surface and/or the tissue surface. When the tissue engaging surface is moveable with respect to the needle, the sensor may measure a translation of the tissue engaging surface. For example, a sensor wheel can be used to engage the needle and measure a translation of the needle by measuring rotation of the sensor wheel. Also other types of sensors may be used, e.g. to measure a distance between a front of the probe housing and the tissue surface using a needle that is stationary with respect to the housing. For example, when the need exists, a depth signal may be calculated by subtracting a measured distance between the front of the housing and the tissue from a known distance between the front of the housing and the needle tip.

By providing the probe housing with a probe head that slides inward with respect to a probe base, the needle may be exposed and pushed into the tissue. By providing a resilient element between the probe head and the probe base a restoring force can be provided to restore a retracted position of the needle inside the probe head in the absence of pressure on the tissue engaging surface.

A second aspect of the present disclosure provides an instrument for measuring a spectral signature of a tissue sample. The instrument comprises the optical probe as described herein and an interrogator configured to provide an input light signal to the optical probe and measure a response light signal from the optical probe as a function of a depth position of the needle in the tissue sample. The optical probe may be connected to the interrogator via appropriate cabling which may include optical and electrical wiring.

By providing the instrument with a z-actuator to control the depth of the needle with respect tot the tissue surface, automatic measurement at different depths can be performed. By providing an xy-actuator to scan a tissue surface, spectral measurements at different locations can be automatically performed.

By providing the instrument with a display screen various measurements may be displayed. By using a digital camera, a picture of the tissue sample can be shown. By generating an image wherein the picture of the tissue sample is overlaid with one or more indicators of tissue measurements performed by the optical probe, the user may gain additional insight. For example, positions of the indicators in the image may correlate with positions of measurements on the tissue sample. For example, different indicators may be shown as a function of the depth dependent spectral measurement for each location. For example, a picture of the tissue engaging surface may be overlaid with visual indicators of the spectral signatures as a function of position on the tissue. When the visual indicators are generated as a function of a margin of healthy tissue surrounding the tumour tissue, the user may relocate portions of the resection tissue where the tumour was optimally removed.

The interrogator is preferably equipped with a light source to provide the input light signal into the optical waveguide for probing inside the tissue sample. The interrogator is preferably equipped with a light sensor to receive a response light signal from the optical waveguide indicative of a response of the tissue sample to the input light signal. To measure a spectral signature, a dispersion or diffraction element may be provided to spectrally resolve the response light signal on the light sensor. A depth control circuit may be used to determine the depth signal and calculate the depth position of the needle tip with respect to the tissue surface. Of course the circuit may be built from suitable hardware and/or software components. Also other circuitry and/or program instructions may be present. For example, an analyser may be configured to determine a plurality of spectral signatures of the tissue sample as a function of the depth position in the tissue sample based on the response light signal as a function of the depth signal. These and other components may be under control of a processor, e.g. controller configured to coordinate a depth of the needle, wherein the controller stores the spectral signature as a function of depth. For example, the controller is configured to store a series of spectral measurements as a function of depth.

A third aspect of the present disclosure provides a method of measuring a tissue sample. The method comprises providing a needle having a needle tip to penetrate a tissue surface and an optical waveguide to transmit light through the needle. The method comprises using an optical interrogator connected to the optical waveguide to perform a series of spectral measurements while penetrating the tissue surface. The method comprises recording the spectral measurements as a function of a depth position of the needle tip relative to the tissue surface.

By calculating an analyte concentration based on a spectral measurement, the measurement can provide distinguishing details about the tissue composition. A relative concentration of a first analyte with respect to a second analyte can be determined by the relative contributions of their spectral signatures in the spectral measurements. In this way a tumour tissue can be distinguished from a healthy tissue. For example, it is found that some types of tumour tissue may have a higher water concentration than healthy tissue. Also other analytes may be used. By calculating the analyte concentration as a function of the depth position, different tissues may be distinguished along a depth of the tissue. In particular, a margin of healthy tissue surrounding tumour can be calculated based on the depth dependent analyte concentration. If insufficient margin is found in a resection specimen this may indicate that the tumour is not optimally removed which may prompt further action.

By performing the spectral measurements only while the needle moves down into the tissue and not during retraction of the needle, the measurements may be more accurate in particular because the tissue is relatively undamaged the first time the needle penetrate the tissue. By using multiple needles at the same time, a tissue surface can be more quickly scanned. For example an array of needles may perform parallel measurements on the tissue at different locations.

A fourth aspect of the present disclosure provides a computer readable medium with software instructions that when executed by an instrument as described herein according cause execution of one or more of the methods as described herein, in particular automated measurement of a tissue sample.

BRIEF DESCRIPTION OF DRAWINGS

These and other features, aspects, and advantages of the apparatus, systems and methods of the present disclosure will become better understood from the following description, appended claims, and accompanying drawing wherein:

DESCRIPTION OF EMBODIMENTS

Figure 1:
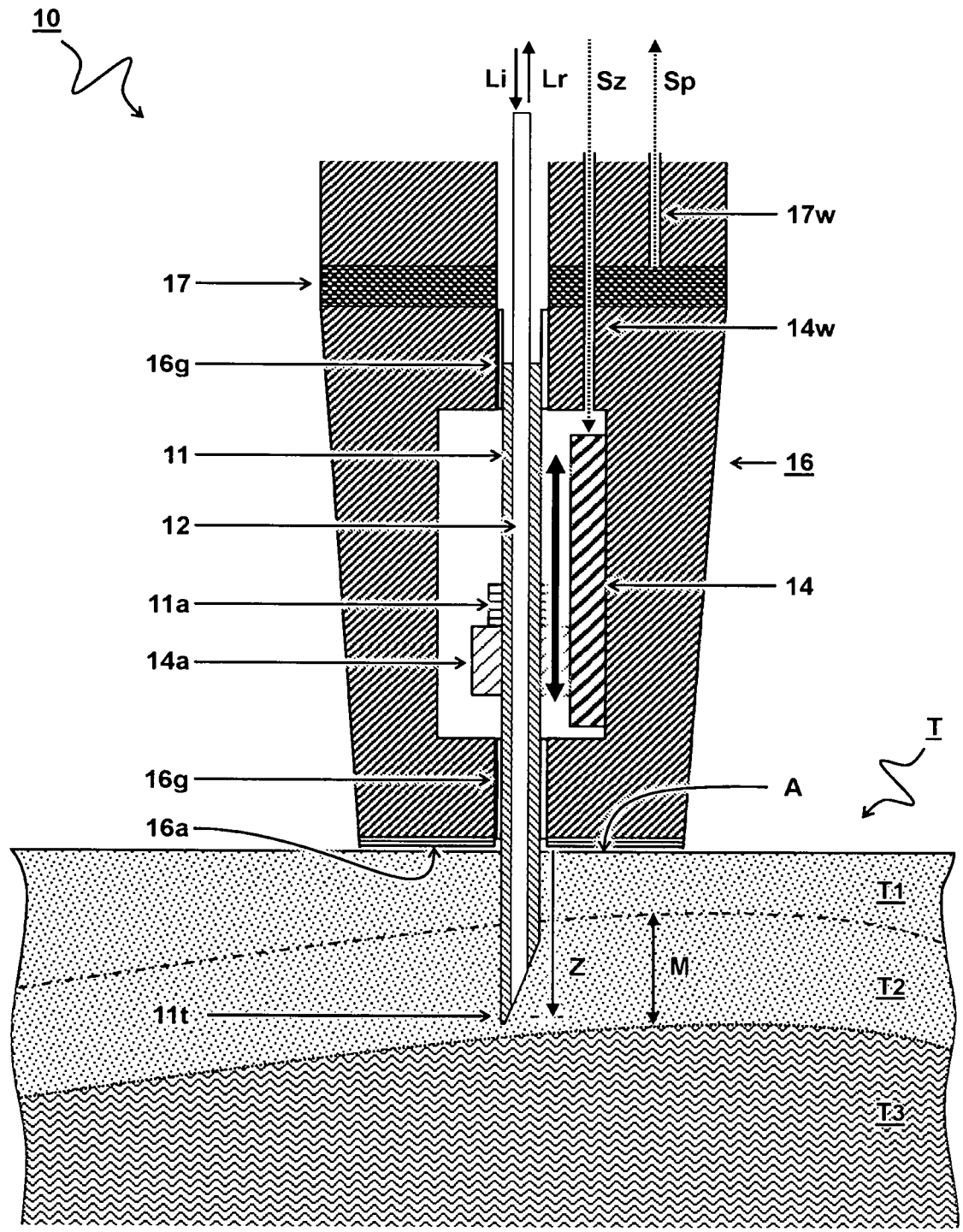
FIG. 1 schematically illustrates a cross-section view of a first embodiment of an optical probe for measuring a tissue sample.

In some instances, detailed descriptions of well-known devices and methods may be omitted so as not to obscure the description of the present systems and methods. Terminology used for describing particular embodiments is not intended to be limiting of the invention. As used herein, the singular forms "a", "an" and "the" are intended to include the plural forms as well, unless the context clearly indicates otherwise. The term "and/or" includes any and all combinations of one or more of the associated listed items. It will be understood that the terms "comprises" and/or "comprising" specify the presence of stated features but do not preclude the presence or addition of one or more other features. It will be further understood that when a particular step of a method is referred to as subsequent to another step, it can directly follow said other step or one or more intermediate steps may be carried out before carrying out the particular step, unless specified otherwise. Likewise it will be understood that when a connection between structures or components is described, this connection may be established directly or through intermediate structures or components unless specified otherwise. All publications, patent applications, patents, and other references mentioned herein are incorporated by reference in their entirety. In case of conflict, the present specification, including definitions, will control.

The invention is described more fully hereinafter with reference to the accompanying drawings, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. The description of the exemplary embodiments is intended to be read in connection with the accompanying drawings, which are to be considered part of the entire written description. In the drawings, the absolute and relative sizes of systems, components, layers, and regions may be exaggerated for clarity. Embodiments may be described with reference to schematic and/or cross-section illustrations of possibly idealized embodiments and intermediate structures of the invention. In the description and drawings, like numbers refer to like elements throughout. Relative terms as well as derivatives thereof should be construed to refer to the orientation as then described or as shown in the drawing under discussion. These relative terms are for convenience of description and do not require that the system be constructed or operated in a particular orientation unless stated otherwise.

FIG. 1 schematically illustrates a cross-section view of a first embodiment of an optical probe 10 for measuring a tissue sample T.

The optical probe 10 comprises a needle 11 having a needle tip 11t formed to penetrate a tissue surface "A". The needle further comprises an optical waveguide 12 arranged to transmit light Li,Lr through the needle 11. The optical probe 10 comprises a probe housing 16 for holding the needle 11. The probe housing 16 comprises an actuator 14 configured to receive a depth signal Sz to determine a depth position z of the needle tip 11t relative to the tissue surface "A". In some embodiments, the actuator may also act as sensor or a sensor can be added to measure the depth position z of the needle.

In one embodiment, the methods of measuring the tissue sample T are performed ex-vivo on a resected tissue specimen. For example the tissue sample T is measured intraoperatively. For example, when the tissue T is excised as a procedure to remove a tumour, the region T1 may correspond to a healthy tissue while the region T3 may correspond to a tumour tissue. The region T2 may be an intermediate region in a margin M where there is a chance that tumour tissue has partly grown into the healthy tissue. For improved chances of success, it is desired to cut out the tumour tissue with a certain margin of healthy tissue around the tumour to prevent recurrence of the tumour.

In one embodiment, the needle 11 comprises one or more optical fibers forming the optical waveguide 12. For example, a needle such as described in WO 2014162289 A1 can be used. In one embodiment, an optical fiber is fixated inside a hypodermic needle, e.g. using epoxy to fill or partly fill the space between the optical fiber and the inner wall of the hypodermic needle. The optical fiber may be inserted until the distal end of the optical fiber is at a defined distance to the tip of the needle. The distance may be chosen such that when the needle is inserted in the tissue there is direct contact between the optical fiber and the tissue. In one embodiment, the distal end of the fiber is polished. The fiber may be flat (end face perpendicular to optical axis of the fiber) or polished at an angle, e.g. flush with the angle of the needle tip. In one embodiment, the proximal fiber end is fixated in a connector, e.g. an SMA-coupler or an FC/PC coupler, and polished flush with respect to connector face, enable butt-coupling to a second optical fiber inserted into a same fiber coupler (commonly used fiber coupling techniques. In one embodiment, a bevel angle of 30°-35° provides a needle which is easy to insert and which provides a low tendency to cause tissue sticking.

Figure 4:
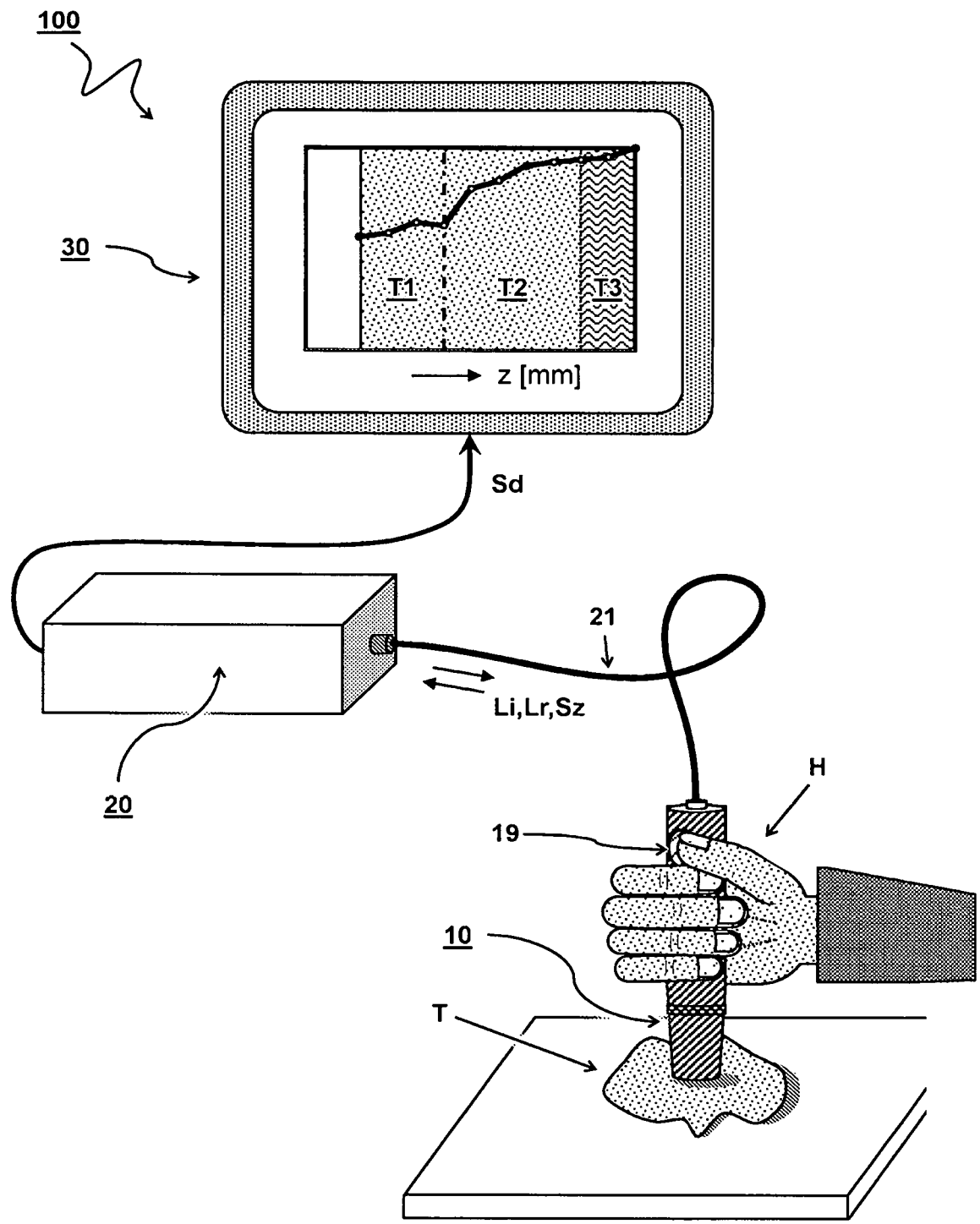
FIG. 4 schematically illustrates a perspective view of a first embodiment of an instrument for measuring a tissue sample.
Figure 5:
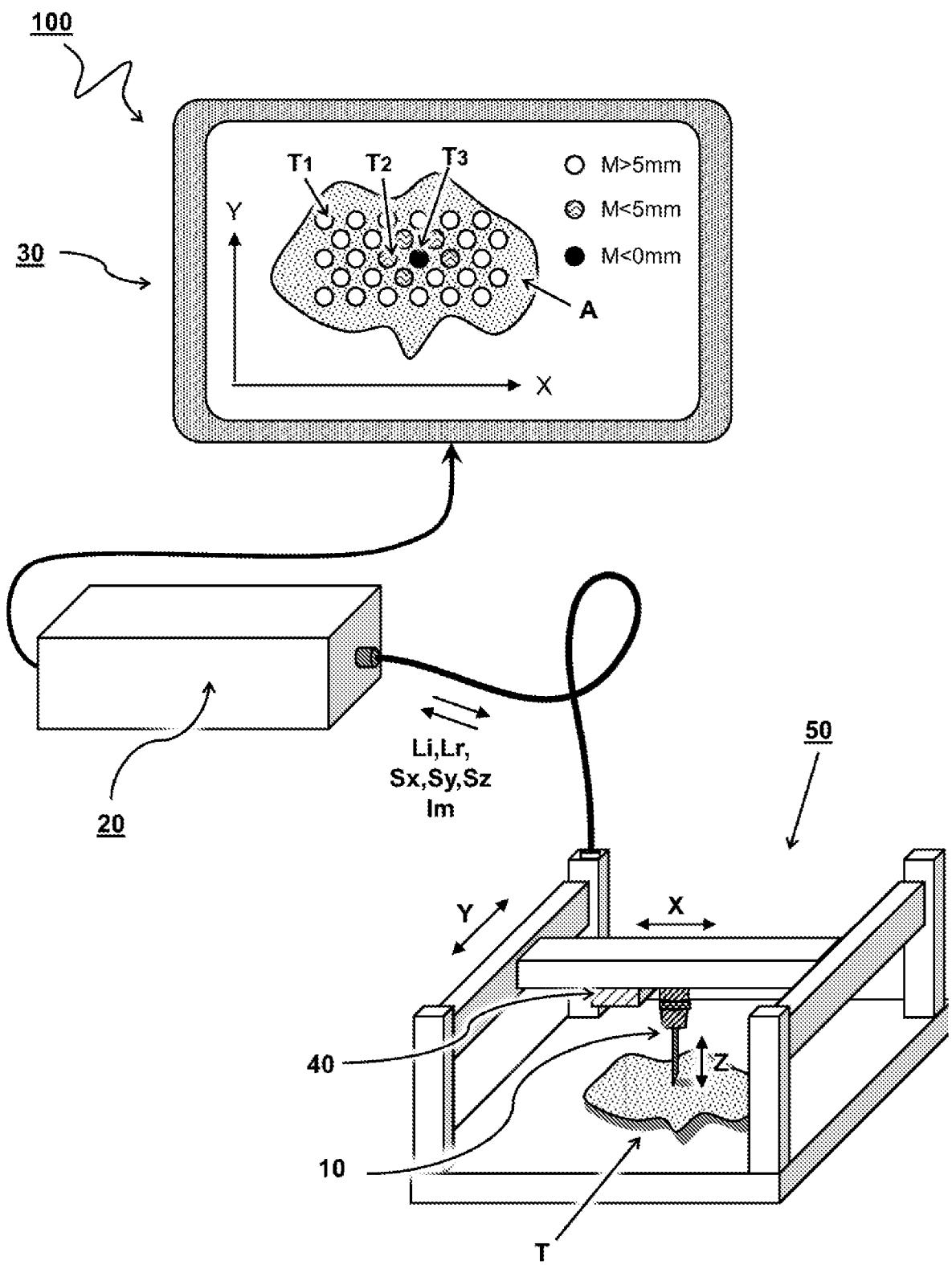
FIG. 5 schematically illustrates a perspective view of a second embodiment of an instrument for measuring a tissue sample.

For example, the optical fiber extends beyond a length of the needle 11 on a distal side of the needle 11 opposite the needle tip 11t to connect to an optical interrogator device (shown e.g. in FIGS. 4 and 5). In one embodiment, the optical fiber is formed to transmit an excitation light signal Li into the tissue sample T and a response Raman spectrum Lr out of the tissue sample T. In another or further embodiment, the optical fiber comprises a core, a cladding and optionally a coating for transmitting light at least in a wavelength range between 600 to 1000 nanometres. Accordingly, the optical fiber is preferably formed to transmit Raman signals through the optical fiber. For example, EP 1 567 852 B1 describes various aspects of using high wavenumber Raman spectroscopy for measuring tissue. In particular, the optical fiber and signal analysis as described in EP 1 567 852 B1 may have advantageous use in the present systems and method.

In one embodiment, the probe housing 16 comprises a tissue engaging surface 16a. In another or further embodiment, the probe housing 16 comprises a needle guiding structure 16g configured to guide the needle 11 transverse to the tissue engaging surface 16a. For example, the depth signal Sz is calculated as a function of a variable distance between the needle tip 11t and the tissue engaging surface 16a. Preferable, the needle guiding structure 16g is configured to slidingly engage the needle. Also other guiding structures can be used, e.g. rollers. In one embodiment, the needle 11 is configured to slide through the needle guiding structure 16g between a retracted position fully inside the probe housing 16 and an extended position out of the probe housing and into the tissue sample T.

In one embodiment, the actuator 14 is configured to actuate the needle 11. Accordingly, the depth signal Sz is an input signal of the actuator 14 to provide an absolute or relative position of the needle tip 11t with respect to the tissue surface "A" and/or the tissue engaging surface 16a. In another or further embodiment, the actuator 14 comprises a translation stage with a moveable stage mount 14a wherein the stage mount 14a is attached to the needle 11 and/or needle mount 11a. In a further embodiment, the probed comprises a depth signal wire 14w configured to transmit the depth signal Sz to the actuator 14 to control actuation of the depth position z of the needle. For example an electrical wire can be used.

In one embodiment, the optical probe 10 comprises a pressure sensor 17 configured to determine a contact between the tissue engaging surface 16a and the tissue surface "A". In another or further embodiment, a pressure signal wire 17w is configured to transmit a pressure signal Sp indicative of the contact between the tissue engaging surface 16a and the tissue surface "A". In another or further embodiment, the actuator 14 is configured to actuate the needle 11 upon detection of contact between the tissue engaging surface 16a and the tissue surface "A".

Figure 2:
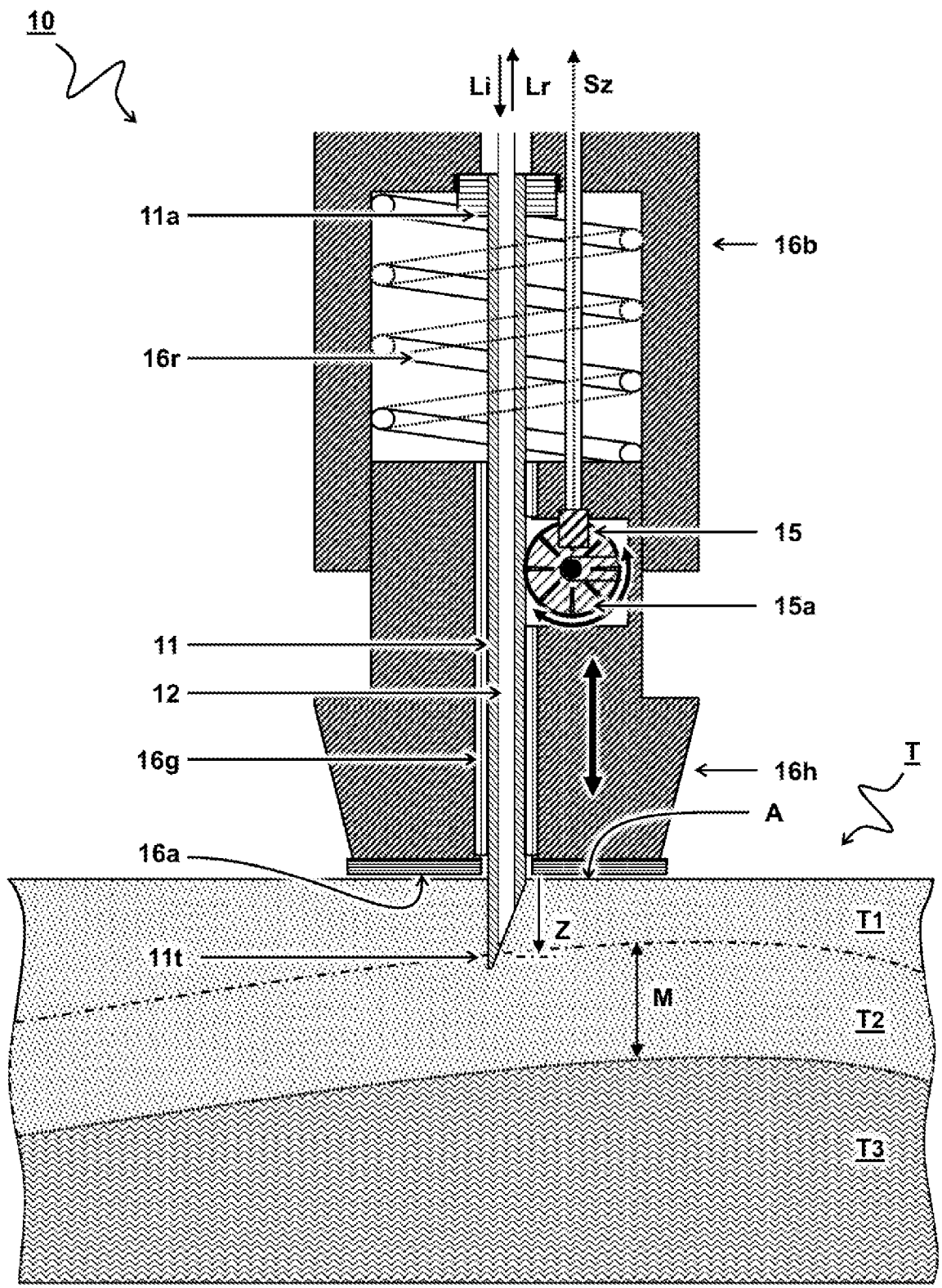
FIG. 2 schematically illustrates a cross-section view of a second embodiment of an optical probe for measuring a tissue sample.

FIG. 2 schematically illustrates a cross-section view of a second embodiment of an optical probe 10 for measuring a tissue sample T.

In the embodiment, the probe housing 16 comprises a sensor 15 configured to generate a depth signal Sz to determine a depth position z of the needle tip 11t relative to the tissue surface "A". Accordingly, the sensor 15 is configured to measure the depth position z of the needle tip 11t. In one embodiment, the depth signal Sz is calculated from an output of the sensor 15 which is configured to measure a translation of the needle 11 relative to the tissue engaging surface 16a and/or the tissue surface "A".

In one embodiment, the tissue engaging surface 16a is moveable with respect to the needle 11. In another or further embodiment, the sensor 15 is configured to measure a translation of the tissue engaging surface 16a. For example, the sensor 15 comprises a sensor wheel 15a configured to engage the needle 11 and measure a translation of the needle 11 by measuring rotation of the sensor wheel 15a. The sensor 15 may e.g. comprise an optical sensor configured to measure passage of light through slots in the rotating wheel. By using variable slots, the direction of rotation can be determined. For example, different slots may have different width and/or different transmission spectra. It will be appreciated that this may allow a fully optical (not electrical) probe wherein both the spectral signature as well as the depth are determined from optical signals. Accordingly, in one embodiment the depth sensor 15 is an optical device.

In one embodiment, the probe housing 16 comprises a probe head 16h and a probe base 16b wherein the tissue engaging surface 16a is disposed on a front of the probe head 16h. In another or further embodiment, the probe head 16h is configured to slide inward with respect to the probe base 16b thereby exposing the needle 11. Preferably, the optical probe 10 comprises a resilient element 16r arranged between the probe head 16h and the probe base 16b and configured to provide a restoring force to restore a retracted position of the needle 11 inside the probe head 16h in the absence of pressure on the tissue engaging surface 16a.

Figure 3:
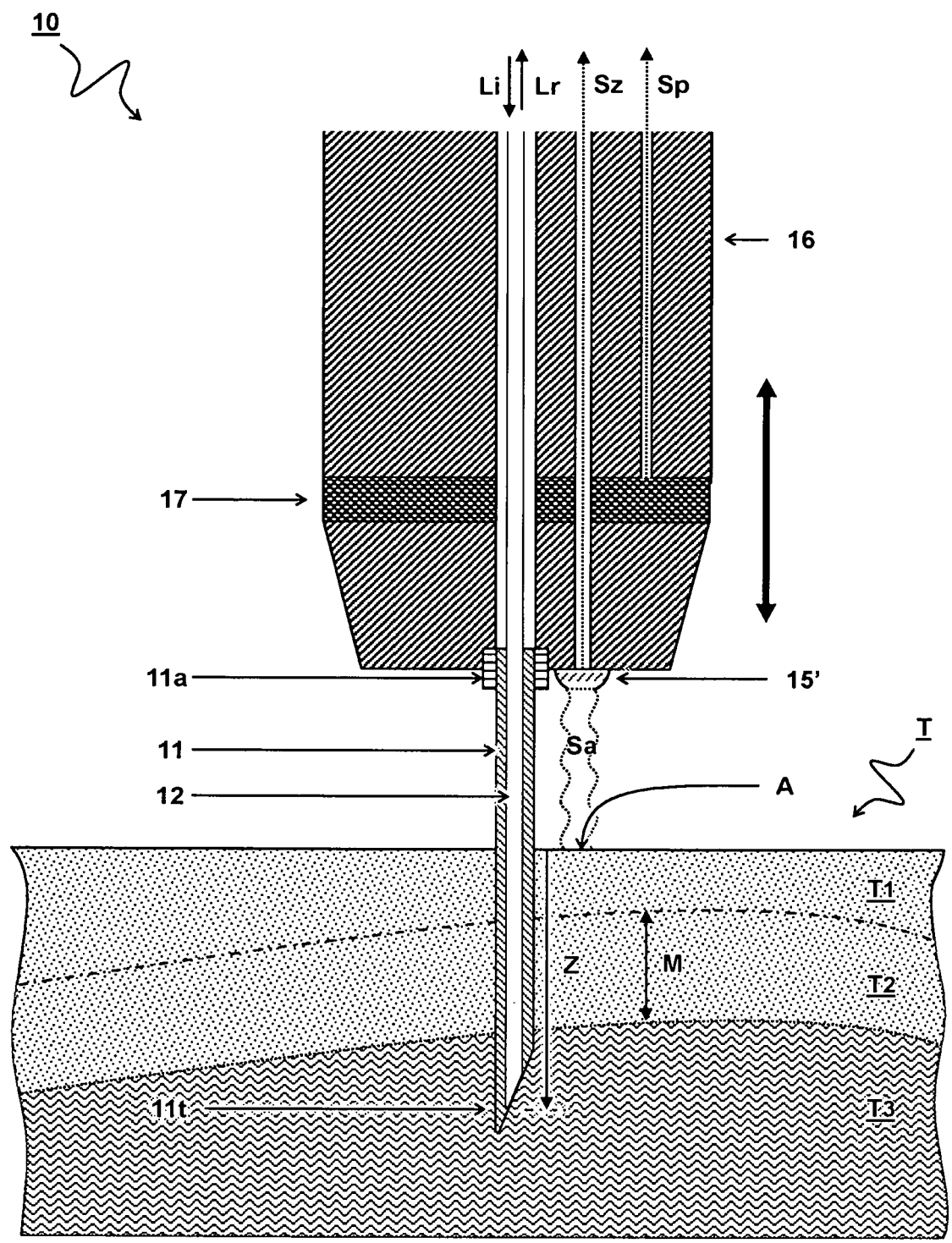
FIG. 3 schematically illustrates a cross-section view of a third embodiment of an optical probe for measuring a tissue sample.

FIG. 3 schematically illustrates a cross-section view of a third embodiment of an optical probe 10 for measuring a tissue sample T.

In one embodiment, a sensor 15' is configured to measure a distance between a front of the probe housing 16 and the tissue surface "A". For example, the depth signal Sz is calculated by subtracting the measured distance from a known distance between the needle tip 11t and the front of the probe housing 16. In another or further embodiment, the sensor 15' is disposed on a front of the probe housing 16 adjacent the needle 11. For example, the sensor 15' may be an optical distance sensor configured to measure the distance to the tissue surface "A" using an optical signal Sa. Also other distance sensors may be used. Alternative or in addition to the distance sensor 15', a pressure sensor 17 can be configured to detect when the needle 11 comes into contact with the tissue surface. Alternatively, or in addition, a contact sensor can be used, e.g. a capacitive sensor connected to the needle to determine contact with the tissue. Also the amount of contact (depth of the needle) may be determined e.g. by measuring capacitance and or conductance. The depth position z can be determined e.g. by measuring and/or controlling the actuated distance from the point of contact with the tissue surface "A". The optical probe 10 can e.g. be used in an automated instrument wherein the whole probe is moved. The needle 11 can be stationary with respect to the probe housing 16, e.g. attached via a needle mount 11a.

Also other combinations and variations of the optical probe 10 are possible. For example, in one embodiment (not shown) the optical probe 10 comprises an array of needles configured to simultaneously perform measurements at different locations over the tissue surface "A". The instrument 100 may also comprise additional actuators, e.g. rollers to rotate the tissue specimen for measuring different sides of the tissue specimen.

FIG. 4 schematically illustrates a perspective view of a first embodiment of an instrument 100 for measuring a tissue sample T.

In one embodiment, the instrument 100 comprises the optical probe 10, e.g. as described herein, and an interrogator 20 configured to provide an input light signal Li to the optical probe 10 and measure a response light signal Lr from the optical probe 10 as a function of a depth position z of the needle in the tissue sample T. In one embodiment, the optical probe 10 is connected to the interrogator 20 via an optical cable configured to transmit the light signals Li,Lr for measuring a spectrum of the tissue sample T. In another or further embodiment, the optical probe 10 is connected to the interrogator 20 via an electrical cable configured to transmit the depth signal Sz for determining a depth position z of the needle corresponding to the measured spectrum. The depth signal may also be transmitted as an optical signal.

In one embodiment, the optical probe 10 comprises a hand grip portion to hold the optical probe 10 by hand (H) and engage the optical probe 10 with the tissue sample T to perform the measurement. Accordingly, the optical probe 10 can be a hand-held device. In another or further embodiment, the optical probe 10 comprises a button 19 to initiate a measurement. For example, the button 19 activates an actuator and/or releases a safety mechanism to allow the needle to extend from the probe housing.

In one embodiment, the instrument 100 comprises or couples to a display screen 30 to display the measurement. In the shown embodiment, the interrogator 20 directly connects to a display screen. Alternatively, or in addition, the interrogator 20 may connect to a computer running software that controls the interrogator 20 and/or receives data output from the interrogator 20. The display screen may be connected to the computer. The computer may also be considered part of the interrogator.

FIG. 5 schematically illustrates a perspective view of a second embodiment of an instrument 100 for measuring a tissue sample T.

In one embodiment, the instrument 100 comprises an actuator table 50 comprising one or more actuators. For example, the instrument 100 comprises a z-actuator configured to control the depth of the needle with respect to the tissue surface to perform automatic measurement at different depths. For example, the instrument 100 comprises an xy-actuator configured to scan a tissue surface and perform spectral measurements at different locations. The actuators may be controlled by the interrogator 20 and/or further hardware e.g. using corresponding control signals Sx,Sy,Sz.

In one embodiment, the instrument 100 comprises a digital camera 40 configured to record and/or transmit a picture "Im" of the tissue sample T under investigation. In another or further embodiment, the interrogator 20 (or computer) is configured to generate an image wherein the picture of the tissue surface "A" is overlaid with one or more indicators T1,T2,T3 of tissue measurements performed by the optical probe 10. For example, a picture of the tissue surface A is overlaid with visual indicators (e.g. color dots T1,T2,T3) of the spectral signatures as a function of position (X,Y) on the tissue. Accordingly, positions of the indicators in the image may correlate with positions of a measurements on the tissue sample T. For example, different indicators may be displayed as a function of a depth dependent spectral measurement. For example, the visual indicators are generated as a function of a margin of healthy tissue surrounding the tumour tissue. In one embodiment, the instrument may provide an option to select regions of interest in the picture for additional measurements. Accordingly, a quick measurement can be taken over the tissue surface followed by a specific measurements at regions of interest.

Figure 6:
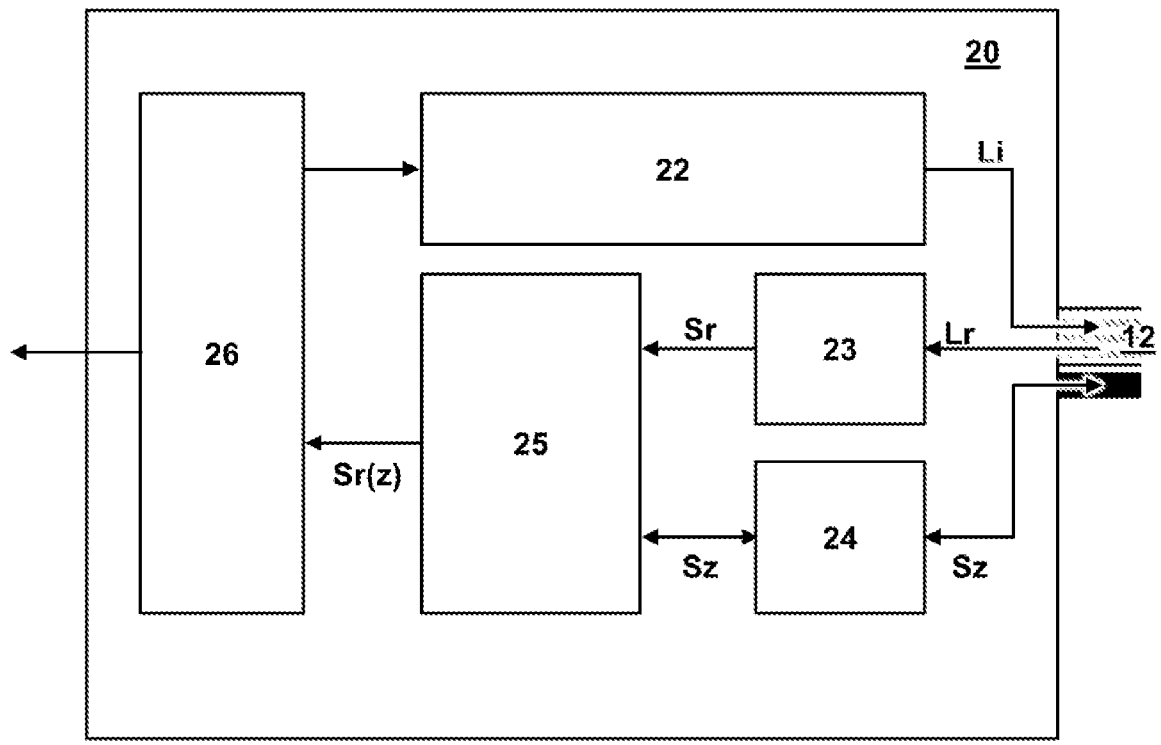
FIG. 6 schematically illustrates a diagram of an embodiment of an interrogator for measuring a tissue sample.

FIG. 6 schematically illustrates a diagram of an embodiment of an interrogator 20 for measuring a tissue sample.

In one embodiment, the interrogator 20 comprises a light source 22 configured to provide the input light signal Li into the optical waveguide 12 for probing inside the tissue sample. For example, the light source 22 may comprise a laser configured to generate a Raman inducing light input signal Li.

In one embodiment, the interrogator 20 comprises a light sensor 23 configured to receive a response light signal Lr from the optical waveguide 12 indicative of a response of the tissue sample T to the input light signal Li. For example, the light sensor 23 may comprise a pixel array to record a light spectrum. In another or further embodiment, the interrogator 20 comprises a dispersion or diffraction element (not shown) to spectrally resolve the response light signal Lr on the light sensor 23.

In one embodiment, the interrogator 20 comprises a depth control circuit 24 configured to determine the depth signal Sz and calculate the depth position z of the needle tip 11$t$ with respect to the tissue surface "A". For example, the circuit 24 may comprise an actuator control to control an actuator attached to the needle. For example, the circuit 24 may comprise a depth sensor readout to receive and/or process sensor signals indicating the depth of the needle.

In one embodiment, the interrogator 20 comprises an analyser 25 configured to determine a plurality of spectral signatures Sr of the tissue sample T as a function of the depth position z in the tissue sample T based on the response light signal Lr as a function of the depth signal Sz. Functionality of the analyser may be provided by software and/or hardware components.

In one embodiment, the interrogator 20 comprises a controller 26 configured to coordinate a depth of the needle, wherein the controller stores the spectral signature as a function of depth. For example, the interrogator 20 comprises or couples to a storage device, e.g. memory, to store data. The controller may be a dedicated or all-purpose processor. The controller may be loaded with software instructions to cause it to perform operational acts in accordance with the present methods and systems.

In one embodiment, the controller 26 is configured to store a series of spectral measurements as a function of depth, wherein each subsequent spectral measurement is only stored if it follows a previous spectral measurement wherein a depth of the needle in the subsequent measurement is equal or larger than a depth z of the needle in the previous measurement. In one embodiment, the spectral measurements are performed only while the needle moves down into the tissue i.e. before the tissue is damaged.

Figure 7:
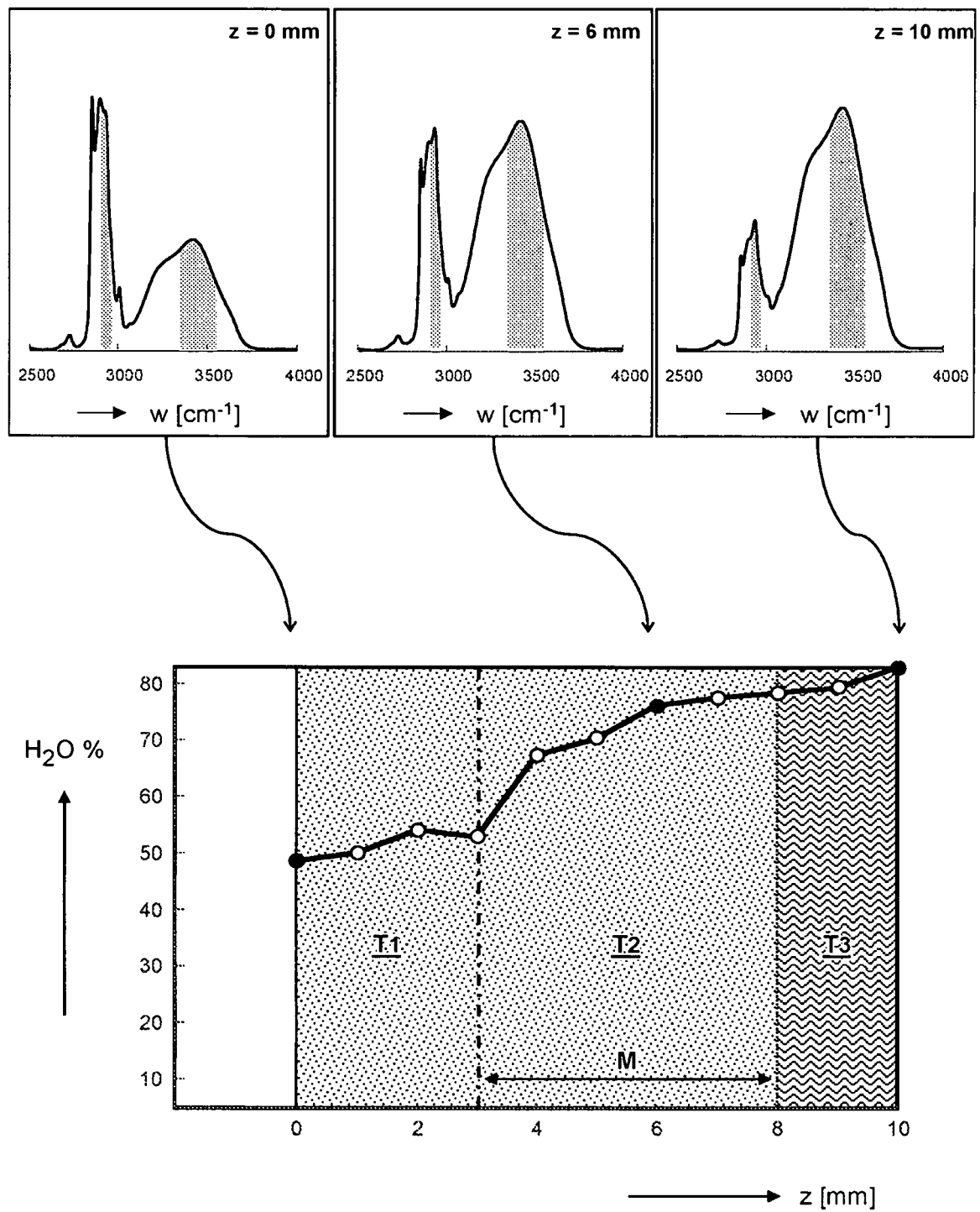
FIG. 7 illustrates (top) Raman spectra of a tissue sample at various depths, and (bottom) a depth dependent water concentration based on the Raman spectra.

FIG. 7 illustrates at the top Raman spectra of a tissue sample at various depths (z), and at the bottom a depth (z) dependent water (H2O) concentration based on the Raman spectra.

For example, the region T1 may correspond to a spectral signature associated with healthy tissue while the region T3 may correspond to a spectral signature associated with tumour tissue. The region T2 may be an intermediate region where there is a chance that tumour tissue has partly grown into the healthy tissue.

The present disclosure enables various methods of measuring a tissue sample. In one embodiment, the method comprises providing a needle having a needle tip to penetrate a tissue surface and an optical waveguide to transmit light through the needle. In another or further embodiment, the method comprises using an optical interrogator connected to the optical waveguide to perform a series of spectral measurements while penetrating the tissue surface. In another or further embodiment, the method comprises recording the spectral measurements as a function of a depth position of the needle tip relative to the tissue surface. Some methods may be partly or wholly embodied as a computer readable medium with software instructions that, when executed by an instrument 100, causes the execution of the methods as described herein.

In one embodiment, the method comprises calculating an analyte concentration based on a spectral measurement. In another or further embodiment, an analyte concentration is calculated as a function of the depth position z. For example, a relative concentration of a first analyte is calculated with respect to a second analyte based on relative contributions of their spectral signatures in the spectral measurements. For example, the analyte is water. In one embodiment, the calculation of water concentration may comprise using the ratio of the Raman bands at 3390 $cm^1$ and 2935 $cm^1$, corresponding to spectral bands of the OH and $CH_3$ stretch vibrations, respectively. Optionally, a background signal may be subtracted from the spectrum before calculating the ratio. For example a procedure for calculating water concentration based on Raman spectra is explained in an article by Caspers et al. (J. Invest. Dermatol. 2001, 3, 434-442) and an article by Wolthuis et al. (J. Anal. Chem. 2001, 73, 3915-3920).

For some types of cancer, a tumour tissue (T3) may be distinguished from a healthy tissue (T1) by an analyte concentration. For example, a tumour tissue T3 may have a higher water concentration than healthy tissue T1. The tissue T2 may be intermediate tissue which may or 15 may not have tumour growth. In one embodiment, a margin "M" (safety distance) around the tumour tissue T3 is calculated based on the depth dependent analyte concentration. For example a safety margin of at least 5 millimeters may be preferable to increase chances that the tumour is completely resected.

For the purpose of clarity and a concise description, features are described herein as part of the same or separate embodiments, however, it will be appreciated that the scope of the invention may include embodiments having combinations of all or some of the features described. For example, while embodiments were shown for various probes, including actuators, sensors, circuitry etcetera, also alternative ways may be envisaged by those skilled in the art having the benefit of the present disclosure for achieving a similar function and result. For example, optical, electrical, and/or mechanical components may be combined or split up into one or more alternative components. For example, while needles where shown with a bevelled angle, also needles with a straight or other formed ending can be used. The various elements of the embodiments as discussed and shown offer certain advantages, such as providing instruments and methods for performing analysis of a depth dependent tissue composition. Of course, it is to be appreciated that any one of the above embodiments or processes may be combined with one or more other embodiments or processes to provide even further improvements in finding and matching designs and advantages. It is appreciated that this disclosure offers particular advantages to inspection of resected tissue specimens, and in general can be applied for any application wherein a tissue composition is to be analysed.

While the present systems and methods have been described in particular detail with reference to specific exemplary embodiments thereof, it should also be appreciated that numerous modifications and alternative embodiments may be devised by those having ordinary skill in the art without departing from the scope of the present disclosure. For example, embodiments wherein devices or systems are disclosed to be arranged and/or constructed for performing a specified method or function inherently disclose the method or function as such and/or in combination with other disclosed embodiments of methods or systems. Furthermore, embodiments of methods are considered to inherently disclose their implementation in respective hardware, where possible, in combination with other disclosed embodiments of methods or systems. Furthermore, methods that can be embodied as program instructions, e.g. on a non-transient computer-readable storage medium, are considered inherently disclosed as such embodiment.

Finally, the above-discussion is intended to be merely illustrative of the present systems and/or methods and should not be construed as limiting the appended claims to any particular embodiment or group of embodiments. The specification and drawings are accordingly to be regarded in an illustrative manner and are not intended to limit the scope of the appended claims. In interpreting the appended claims, it should be understood that the word "comprising" does not exclude the presence of other elements or acts than those listed in a given claim; the word "a" or "an" preceding an element does not exclude the presence of a plurality of such elements; any reference signs in the claims do not limit their scope; several "means" may be represented by the same or different item(s) or implemented structure or function; any of the disclosed devices or portions thereof may be combined together or separated into further portions unless specifically stated otherwise. The mere fact that certain measures are recited in mutually different claims does not indicate that a combination of these measures cannot be used to advantage. In particular, all working combinations of the claims are considered inherently disclosed.

The invention claimed is:

1. An optical probe for measuring a resection margin of a tissue sample to assess a sufficiency of the resection margin, the optical probe comprising
a needle having a needle tip formed to penetrate a tissue surface and a single optical waveguide disposed inside the needle and arranged to transmit light through the needle, wherein a distal end of the single optical waveguide is disposed at the needle tip to allow light to exit the distal end at the needle tip, and re-enter the distal end at the needle tip after having exclusively interacted with a region of the tissue sample substantially localized at a depth position of the needle tip to measure the resection margin; and
a probe housing for holding the needle wherein the probe housing comprises a tissue engaging surface and a needle guiding structure configured to guide the needle transverse to the tissue engaging surface, wherein the probe housing further comprises at least one of an actuator configured to receive a depth signal as input to set the depth position of the needle tip with respect to the tissue engaging surface, or a sensor configured to generate the depth signal by measuring a translation of the needle relative to the tissue engaging surface, wherein the depth signal is calculated as a function of a variable distance between the needle tip and the tissue engaging surface to assess the sufficiency of the resection margin.

2. The optical probe according to claim 1, wherein the needle is configured to slide through the needle guiding structure between a retracted position fully inside the probe housing and an extended position out of the probe housing and into the tissue sample.

3. The optical probe according to claim 1, comprising a contact or pressure sensor configured to determine a contact between the tissue engaging surface and the tissue surface.

4. The optical probe according to claim 1, wherein the probe housing comprises a probe head and a probe base, wherein a tissue engaging surface is disposed on a front of the probe head, wherein the probe head is configured to slide inward with respect to the probe base thereby exposing the needle.

5. The optical probe according to claim 1, wherein the optical probe comprises a hand grip portion to hold the optical probe by hand and engage the optical probe with the tissue sample to perform the measurement, wherein the optical probe comprises a button to initiate a measurement.

6. The optical probe according to claim 1 further comprising
an interrogator configured to provide an input light signal and measure a response light signal as a function of a depth position of the needle in the tissue sample.

7. The optical probe according to claim 6, wherein the interrogator comprises an analyzer configured to measure a series of spectral signatures of the tissue sample as a function of the depth position in the tissue sample based on the response light signal as a function of the depth signal.

8. The optical probe according to claim 6, comprising a z-actuator configured to control the depth of the needle with respect to the tissue surface to perform automatic measurement at different depths and an xy-actuator configured to scan a tissue surface and perform spectral measurements at different locations.

9. The optical probe according to claim 6, comprising a digital camera configured to record a picture of the tissue sample, wherein the interrogator is configured to generate an image wherein the picture of the tissue sample is overlaid with one or more indicators of tissue measurements performed by the optical probe, wherein positions of the indicators in the image correlate with positions of a measurements on the tissue sample, wherein different indicators are generated as a function of a depth dependent spectral measurement.

10. A method of ex-vivo measuring a resected tissue sample to assess a sufficiency of a resection margin, the method comprising
providing a probe housing comprising a tissue engaging surface and a needle guiding structure configured to guide a needle transverse to the tissue engaging surface, the needle having a needle tip to penetrate a tissue resection surface of the resected tissue sample and a single optical waveguide to transmit light through the needle, wherein the optical waveguide ends at the needle tip to emit the light to parts of the tissue sample surrounding the needle tip and to collect resulting light that has substantially only interacted with the parts of the tissue sample surrounding the needle tip, wherein the probe housing comprises at least one of an actuator or a sensor configured to receive or generate a depth signal indicative of a depth position of the needle tip relative to the tissue engaging surface;

using an optical interrogator connected to the optical waveguide to perform a series of spectral measurements while penetrating the tissue resection surface by guiding the needle through the needle guiding structure transverse to the tissue engaging surface while receiving or generating the depth signal indicative of the depth position of the needle tip relative to the tissue engaging surface;

recording the spectral measurements as a function of a depth position of the needle tip relative to the tissue resection surface based on the depth signal indicative of the depth position of the needle tip relative to the tissue engaging surface; and determining a resection margin of healthy tissue surrounding tumour tissue based on the spectral measurements as a function of the depth position of the needle tip relative to the tissue resection surface to assess the sufficiency of the resection margin.

11. The method according to claim 10, wherein the spectral measurements are performed only while the needle moves down into the resected tissue sample.

12. A non-transitory computer readable medium with software instructions that when executed by an instrument for measuring a spectral signature of a tissue sample causes the instrument to provide a needle tip to penetrate a tissue surface of the tissue sample, while a single optical waveguide transmits light through the needle; wherein the instrument performs a series of spectral measurements while penetrating the tissue surface; records spectral measurements as a function of a depth position of the needle tip relative to the tissue surface; and determines a resection margin of healthy tissue surrounding tumour tissue based on the spectral measurements as function of the depth position to assess a sufficiency of the resection margin.

13. The optical probe according to claim 1, wherein the tissue engaging surface is planar, wherein the needle guiding structure is fixedly arranged in the housing normal to a reference plane formed by the planar tissue engaging surface, to guide the needle perpendicular to the tissue engaging surface.

14. The method according to claim 10, comprising generating a visual indicator as a function of the resection margin.

15. The method according to claim 10, wherein the needle holds a single optical waveguide disposed inside, wherein a distal end of the single optical waveguide is disposed at the needle tip to have the light exiting and re-entering the distal end exclusively to interact with a local region of the tissue sample at the needle tip.

* * * * *